(12) United States Patent
Oguchi et al.

(10) Patent No.: US 7,445,790 B2
(45) Date of Patent: Nov. 4, 2008

(54) EXTERNAL PREPARATIONS FOR SKIN

(75) Inventors: Nozomi Oguchi, Yokohama (JP); Reiji Miyahara, Yokohama (JP); Hiroyuki Kakoki, Yokohama (JP); Takayuki Omura, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 770 days.

(21) Appl. No.: 10/513,823

(22) PCT Filed: May 7, 2003

(86) PCT No.: PCT/JP03/05701

§ 371 (c)(1),
(2), (4) Date: Nov. 9, 2004

(87) PCT Pub. No.: WO03/094865

PCT Pub. Date: Nov. 20, 2003

(65) Prior Publication Data

US 2005/0180931 A1 Aug. 18, 2005

(30) Foreign Application Priority Data

May 9, 2002 (JP) .............................. 2002-134438
May 20, 2002 (JP) .............................. 2002-144565

(51) Int. Cl.
*A61K 8/02* (2006.01)
*A61K 31/235* (2006.01)

(52) U.S. Cl. ...................................... 424/401; 514/544

(58) Field of Classification Search ................. 424/401; 514/544

See application file for complete search history.

(56) References Cited

U.S. PATENT DOCUMENTS

| 4,168,248 A | 9/1979 | Kulka |
| 6,051,211 A | 4/2000 | Hansenne et al. |
| 2002/0035046 A1 | 3/2002 | Lukenbach et al. |

FOREIGN PATENT DOCUMENTS

| JP | H07-238296 A | 9/1995 |
| WO | WO 00/54741 | 9/2000 |
| WO | WO 01/55128 A1 | 8/2001 |
| WO | WO 01/74294 A2 | 10/2001 |
| WO | WO 01/97768 A | 12/2001 |
| WO | WO 02/38537 A1 | 5/2002 |
| WO | WO 02/43685 A2 | 6/2002 |

OTHER PUBLICATIONS

Journal of Investigative Dermatology, vol. 86, No. 2, pp. 208-212 (1986) "A Model For Quantifying Absorption through Abnormal Skin", by Robert C. Scott, Ph.D., and Paul H. Dugard, Ph.D., p. 208 under "Test Chemicals".

*Primary Examiner*—Johann Richter
*Assistant Examiner*—Konata M. George
(74) *Attorney, Agent, or Firm*—Townsend & Banta

(57) ABSTRACT

The present invention is a skin treatment composition that characteristically contains an alkyl benzoate represented by the following general formula (1).

This provides a skin treatment composition that gives a refreshing sensation at the time of application and can contain drugs and ultraviolet absorbents in a stable manner.

Also, the present invention is a sunblock water-in-oil type emulsified cosmetic characteristically comprising an ester bond product of polyhydroxystearic acid represented by the following general formulas (2) or (3), alkyl benzoate represented by the following general formula (1), and an ultraviolet absorbent.

This provides a sunblock cosmetic consisting of a water-in-oil type emulsified composition that can contain an ultraviolet absorbent in a stable manner and exhibits a superior usability.

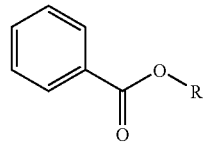 (1)

(In this formula, R denotes a branched or straight chain alkyl group having 8-15 carbon atoms.)

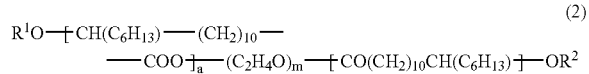 (2)

(In this formula, $R^1$ and $R^2$ denote, independently of each other, a hydrogen atom or a lower alkyl group having 1-6 carbon atoms, a+b denotes an integer 1-30, and m denotes an integer 10-200.)

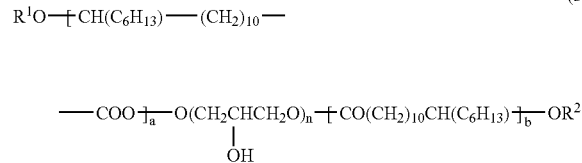 (3)

(In this formula, $R^1$ and $R^2$ denote, independently of each other, a hydrogen atom or a lower alkyl group having 1-6 carbon atoms, a+b denotes an integer 1-30, and n denotes an integer 1-30.)

2 Claims, 3 Drawing Sheets

EXTERNAL PREPARATIONS FOR SKIN

TECHNICAL FIELD

The present invention relates to a skin treatment composition. More specifically, the present invention relates to a skin treatment composition that gives a refreshing sensation at the time of application and contains an oil component that can sufficiently dissolve slightly soluble ultraviolet absorbents and drugs.

The present invention relates to a sunblock water-in-oil (W/O) type emulsified cosmetic. More specifically, it relates to a water-in-oil type emulsified sunblock cosmetic that is not sticky, gives a superior refreshing sensation at the time of application, and can contain slightly soluble ultraviolet absorbents in a stable manner.

BACKGROUND ART

Many silicone oils that give a refreshing sensation at the time of application have been developed and used in skin treatment compositions.

However, since ultraviolet absorbents and drugs do not dissolve well in silicone oils, the addition of hydrocarbon oil components in which drugs and ultraviolet absorbents dissolve well has been desired.

While the hydrocarbon oil components dissolve drugs and ultraviolet absorbents well, they have a problem in that stickiness tends to result with higher blend ratios.

In view of the aforementioned problem, the inventors conducted earnest research and discovered that alkyl benzoate having a specific structure can be added to a skin treatment composition to provide a skin treatment composition that gives a superior refreshing sensation at the time of application, and can contain drugs and ultraviolet absorbents in a stable manner, and thus completed the present invention.

The object of the present invention is to provide a skin treatment composition that gives a superior refreshing sensation at the time of application and can contain slightly soluble ultraviolet absorbents and drugs in a stable manner.

In a sunblock cosmetic consisting of a water-in-oil type emulsified composition, the oil phase is the continuous phase (outer phase). Therefore, compared with a sunblock cosmetic consisting of a oil-in-water type emulsified composition, it has a higher resistance to microorganisms. Also, at the time of application, it leaves an oil film with a low moisture permeability that protects the skin from drying for a long time. Furthermore, it doesn't re-emulsify easily when exposed to water in situations including bathing, washing/cleaning, and perspiration. For these reasons, it is used as a base agent in sunblock cosmetics.

However, conventional sunblock cosmetics consisting of a water-in-oil type emulsified composition must dissolve a large amount of a highly polar ultraviolet absorbent in the oil phase, resulting in separation and aggregation over a period of time; hence there is the problem of poor long term stability.

Also, in terms of usability, compared with a oil-in-water type sunblock cosmetic, it has problems such as stickiness, oiliness, and poor spreadability.

In view of the aforementioned problems, what has been desired is the development of an oil component that has a superior ability to dissolve a highly polar ultraviolet absorbent and a water-in-oil type emulsification base agent that can stably emulsify the oil phase containing an ultraviolet absorbent.

In view of the aforementioned problem, the inventors conducted earnest research and discovered that alkyl benzoate having a specific structure can be used as an oil component to dissolve the ultraviolet absorbent and an ester bond product of polyhydroxystearic acid having a specific structure can be used for the emulsifier to prepare a water-in-oil type emulsified composition that gives a refreshing sensation without stickiness at the time of application and has superior long term stability, and thus completed the present invention.

The object of the present invention is to provide a sunblock cosmetic consisting of a water-in-oil type composition that is not sticky, gives a refreshing sensation at the time of application, and can stably contain a highly polar ultraviolet absorbent, which has been difficult to introduce in a stable manner.

DISCLOSURE OF INVENTION

[Invention Defined in Claims 1-2]

That is, the present invention provides a skin treatment composition that characteristically contains an alkyl benzoate represented by the following general formula (1):

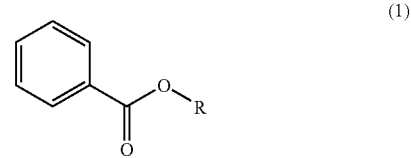

(1)

(In this formula, R denotes a branched or straight chain alkyl group having 8-10 carbon atoms.)

Also, the present invention provides the aforementioned skin treatment composition wherein the compound represented by the aforementioned general formula (1) is 3,7-dimethyloctyl benzoate.

[Invention Defined in Claims 3-7]

That is, the present invention provides a sunblock water-in-oil type emulsified cosmetic characteristically comprising an ester bond product of polyhydroxystearic acid represented by the following general formula (2), alkyl benzoate represented by the following general formula (1), and an ultraviolet absorbent.

(2)

(In this formula, $R^1$ and $R^2$ denote, independently of each other, a hydrogen atom or a lower alkyl group having 1-6 carbon atoms, a+b denotes an integer 1-30, and m denotes an integer 10-200.)

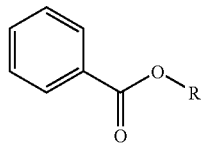

(1)

(In this formula, R denotes a branched or straight chain alkyl group having 8-15 carbon atoms.)

Also, the present invention provides a sunblock water-in-oil type emulsified cosmetic characteristically comprising an ester bond product of polyhydroxystearic acid represented by the following general formula (3), alkyl benzoate represented by the following general formula (1), and an ultraviolet absorbent.

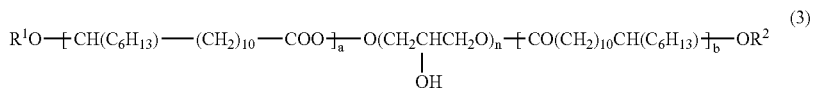

(3)

(In this formula, $R^1$ and $R^2$ denote, independently of each other, a hydrogen atom or a lower alkyl group having 1-6 carbon atoms, a+b denotes an integer 1-30, and n denotes an integer 1-30.)

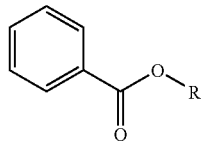

(1)

(In this formula, R denotes a branched or straight chain alkyl group having 8-15 carbon atoms.)

Furthermore, the present invention provides a sunblock water-in-oil type emulsified cosmetic characteristically comprising an ester bond product of polyhydroxystearic acid represented by the following general formulas (2) and (3), alkyl benzoate represented by the following general formula (1), and an ultraviolet absorbent.

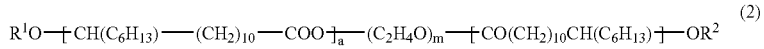

(2)

(In this formula, $R^1$ and $R^2$ denote, independently of each other, a hydrogen atom or a lower alkyl group having 1-6 carbon atoms, a+b denotes an integer 1-30, and m denotes an integer 10-200.)

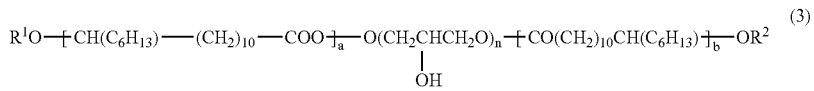

(3)

(In this formula, $R^1$ and $R^2$ denote, independently of each other, a hydrogen atom or a lower alkyl group having 1-6 carbon atoms, a+b denotes an integer 1-30, and n denotes an integer 1-30.)

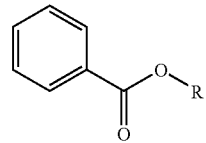

(1)

(In this formula, R denotes a branched or straight chain alkyl group having 8-15 carbon atoms.)

Also, the present invention provides a sunblock water-in-oil type emulsified cosmetic wherein R in the compound represented by the aforementioned general formula (1) denotes a branched or straight chain alkyl group having 8-10 carbon atoms.

Furthermore, the present invention provides the aforementioned sunblock water-in-oil type emulsified cosmetic additionally containing an ultraviolet scattering agent.

BEST MODE FOR CARRYING OUT THE INVENTION

Figure 1:
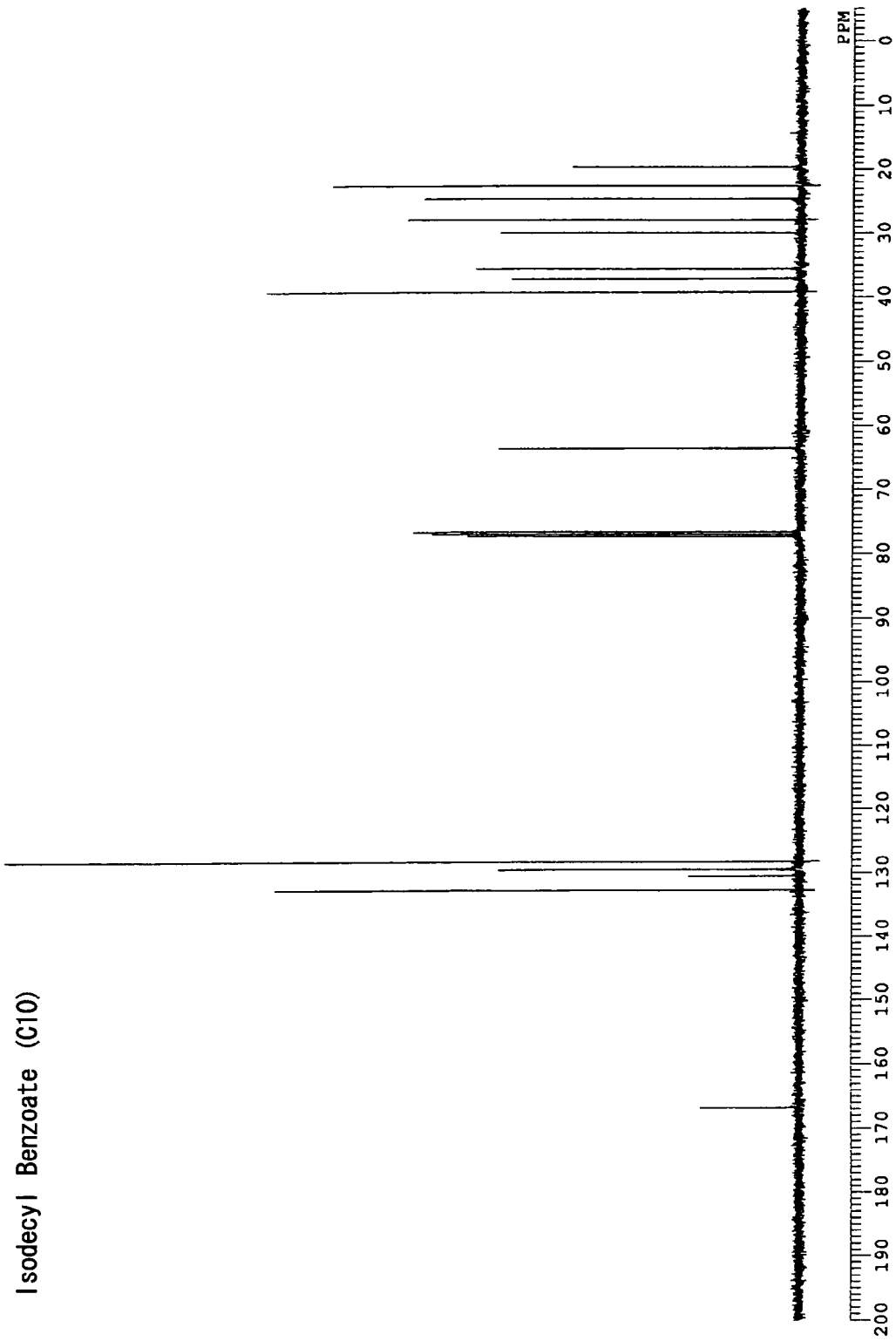
FIG. 1 shows a $^{13}$C NMR spectrum of synthesis example 1.

The present invention is described in detail below.

[Invention Defined in Claims 1-2]

In general formula (1), R denotes a branched or straight chain alkyl group having 8-10 carbon atoms; preferable are branched alkyl groups having 8-10 carbon atoms, and more preferable are branched alkyl groups having 10 carbon atoms.

If R is an alkyl group having seven or less carbon atoms, then volatility and odor cause problems. If R is an alkyl group having 11 or more carbon atoms, then the refreshing sensation at the time of application is degraded, which is not preferable.

Specific examples of the alkyl benzoate that satisfies general formula (1) include octyl benzoate, 2-ethylhexyl benzoate, 3,5,5-trimethylhexyl benzoate, and 3,7-dimethyloctyl benzoate. Of these, 3,7-dimethyloctyl benzoate is particularly preferable because of the sensation at the time of application, solubility of ultraviolet absorbents and drugs, and odorlessness; it gives a skin treatment composition that gives a superior refreshing sensation on the skin and can easily contain ultraviolet absorbents and drugs.

The alkyl benzoate of general formula (1) can be prepared by reacting an alcohol having an alkyl group with a target number of carbon atoms and benzoyl chloride in the presence of triethylamine, using chloroform as the solvent; the reaction formula is shown below and the yield is 90% or higher.

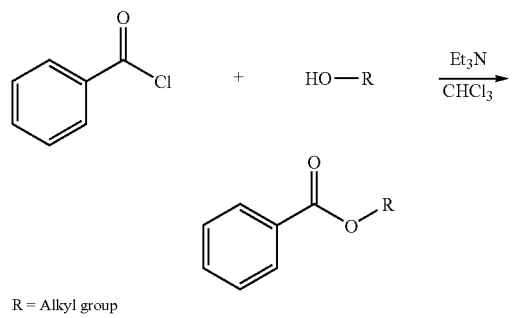

R = Alkyl group

The blend ratio of the alkyl benzoate in the skin treatment composition is not limited in particular. The blend ratio is usually 0.001-50% (mass percentage), preferably 0.1-30.0% (mass percentage), of the total amount of the skin treatment composition. If it is less than 0.001%, then the effect of the addition is not manifested; if it is more than 50.0%, then a sticky sensation may result after application.

The skin treatment composition of the present invention is prepared by blending the aforementioned essential ingredient into an existing skin treatment composition base agent. In addition to the aforementioned essential ingredients, other ingredients used in skin treatment compositions can be blended as necessary in the skin treatment composition of the present invention; examples of such ingredients include powder ingredients, liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, ultraviolet absorbents, sequestering agents, lower alcohols, polyhydric alcohols, sugars, amino acids, organic amines, polymer emulsions, pH adjusting agents, skin nutrients, vitamins, antioxidants, antioxidation assistants, perfumes, and water; and the skin treatment composition can be prepared for the target formulation with a conventional method. Specific ingredients which can be blended in are listed below. The skin treatment composition of the present invention can be prepared by blending the aforementioned essential ingredients and any one, two or more of the following ingredients.

Examples of the ultraviolet absorbents include the following ultraviolet absorbents.

A: Triazine-type Ultraviolet Absorbents

For example, bisresorsinyl triazine. More specifically, bis{[4-(2-ethylhexyloxy)-2-hydroxy]phenyl}-6-(4-methoxyphenyl)1,3,5-triazine, 2,4,6-tris{4-(2-ethylhexyloxycarbonyl)anilino}1,3,5-triazine, etc.

B: Benzoic Acid-type Ultraviolet Absorbents

For example, p-aminobenzoic acid (hereafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester.

C: Anthranilic Acid-type Ultraviolet Absorbents

For example, homo mentyl-N-acetyl anthranilate.

D: Salicylic Acid-type Ultraviolet Absorbents

For example, amyl salicylate, mentyl salicylate, homo mentyl salicylate, octyl salicylate, phenyl salicylate, benzyl salicylate, and p-isopropanol phenyl salicylate.

E: Cinnamic Acid-type Ultraviolet Absorbents

For example, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethyl hexanoyl-di-p-methoxy cinnamate.

F: Other Ultraviolet Absorbents

For example, 3-(4'-methylbenzylidene)-d, 1-camphor, 3-benzylidene-d, 1-camphor, 2-phenyl-5-methyl benzoxazol, 2-(2'-hydroxy-5'-methylphenyl) benzotriazol, 2-(2'-hydroxy-5'-t-octylphenyl) benzotriazol, 2-(2'-hydroxy-5'-methylphenyl benzotriazol, dibenzaladine, dianisoylmethane, and 4-methoxy-4'-t-butyl dibenzoyl-methane, 5-(3,3-dimethyl-2-norbornylidene)-3-pentane-2-one.

Examples of the powder ingredients include inorganic powders (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstic acid metal salt, magnesium, silica, zeolite, barium sulfate, firing calcium sulfate (calcined gypsum), calcium phosphate, fluorine-apatite, hydroxy apatite, ceramic powder, metallic soaps (for example, myristic acid zinc, calcium palmitate, and aluminum stearate), and boron nitride; organic powders (for example, polyamide resin powder (nylon powder), polyethylene powder, poly methyl methacrylate powder, polystyrene powder, powders of copolymer resin of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and loess); inorganic black pigments (for example, black iron oxide and low oxides of titanium); inorganic purple pigments (for example, manganese violet, cobalt violet); inorganic green pigments (for example, chromium oxide, chromium hydroxide, and cobalt titanate); inorganic blue pigments (for example, ultramarine blue and Berlin blue); pearl pigment (for example, titania coated mica, titania coated bismuth oxychloride, titania coated talc, coloration titania coated mica, bismuth oxychloride, fish scale flakes); metal powder pigments (for example, aluminium powder, copper powder); organic pigments such as Zr, barium or aluminium rake (for example, organic pigments such as red 201, red 202, red 204, red 205, red 220, red 226, red 228, red 405, orange 203, orange 204, yellow 205, yellow 401 and blue 404, as well as red 3, red 104, red 106, red 227, red 230, red 401, red 505, orange 205, yellow 4, yellow 5, yellow 202, yellow 203, green 3 and blue 1; and natural colors (for example, chlorophyll and β-carotene).

Examples of the liquid fats and oils include avocado oil, tsubaki oil, turtle fatty acid, macademia nut oil, corn oil, mink oil, olive oil, rapeseed oil, egg yolk oil, sesame oil, persic oil, wheat germ oil, sasanqua oil, castor oil, linseed oil, safflower oil, cotton seed oil, perilla oil, soybean oil, peanut oil, tea seed oil, Japanese nutmeg oil, rice bran oil, Chinese gimlet oil, Japanese gimlet oil, jojoba oil, germ oil, and triglycerin.

Examples of the solid fats and oils include cacao butter, coconut oil, hydrogenated coconut oil, palm oil, palm kernel oil, Japanese core wax nucleus oil, hydrogenated oil, Japanese core wax, and hydrogenated castor oil.

Examples of the waxes include beeswax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin ethyl alcohol ether.

Examples of the hydrocarbon oils include liquid petrolatum, ozocerite, squalane, pristane, paraffin, ceresin, squalene, petrolatum, and microcrystallin wax.

Examples of the higher fatty acids include lauric acid, myristic acid, palmitic acid, stearic acid, behenic acid, oleic acid, undecylenic acid, tall oil fatty acid, isostearic acid, linolic acid, linoleic acid, eicosapentaenoic acid (EPA), and docosahexaenoic acid (DHA).

Examples of the higher alcohols include straight chain alcohols (for example, lauryl alcohol, cetyl alcohol, stearyl alcohol, behenyl alcohol, myristyl alcohol, oleyl alcohol, and cetostearyl alcohol) and branched chain ethyl alcohols (for example, mono stearyl glycerin ether (batyl alcohol), 2-decyltetradecynol, lanolin alcohol, cholesterol, phytosterol, hexyl dodecanol, iso stearyl alcohol, and octyl dodecanol).

Examples of the ester oils include isopropyl myristate, cetyl octanoate, octyl dodecyl myristate, isopropyl palmitate, butyl stearate, hexyl laurate, myristil myristate, decyl oleate, dimethyl hexyl decyl octanoate, cetyl lactate, myristil lactate, lanolin acetate, iso cetyl stearate, iso cetyl isostearate, cholesteryl hydroxy 12-stearate, ethylene glycol di-2-ethylhexanoate, dipentaerythritol fatty acid ester, n-alkylene glycol monoisostearate, neopentyl glycol dicaprate, diisostearyl malate, glyceryl di-2-heptylundecanoate, trimethylolpropane tri-2-ethylhexanoate, trimethylolpropane triisostearate, tetra-2-pentaerythritol ethylhexanoate, glycerin tri-2-ethylhexanoate, glyceryl trioctanoate, glycerin triisopalmitate, trimethylolpropane triisostearate, cetyl 2-ethyl hexanoate, 2-ethylhexyl palmitate, glycerin trimyristate, tri-2-heptyl undecanoic acid glyceride, methyl castor oil fatty acid, oleyl oleate, aceto glyceride, 2-heptyl undecyl palmitate, diisobutyl adipate, 2-octyldodecyl N-lauroyl-L-glutamate, di-2-heptyl undecyl adipate, ethyl laurate, di-2-ethylhexyl sebacate, 2-hexyl decyl myristate, 2-hexyldecyl palmitate, 2-hexyl decyl adipate, diisopropyl sebacate, 2-ethylhexyl succinate, and triethyl citrate.

Examples of the silicone oils include chain polysiloxanes (for example, dimethylpolysiloxane, methylphenyl polysiloxane, and diphenyl polysiloxane); ring polysiloxanes (for example, octamethylcyclotetrasiloxane, decamethyl cyclopenta siloxane, and dodecamethyl cyclohexa siloxane), silicone resins forming a three-dimensional network structure, silicone rubbers, and various modified polysiloxanes (amino-modified polysiloxane, polyether-modified polysiloxane, alkyl-modified polysiloxane, and fluorine-modified polysiloxane).

Examples of the anionic surfactants include fatty acid soaps (for example, sodium laurate and sodium palmitate); higher alkyl sulfuric ester salts (for example, sodium lauryl sulfate and potassium laurylsulfate); alkylether sulfuric ester salts (for example, POE-triethanolamine laurylsulfate and sodium POE-lauryl sulfate); N-acyl sarcosinic acids (for example, sodium N-lauroyl sarcosinate); higher fatty acid amidosulfonic acid salts (for example, sodium N-myristoyl-N-methyl taurate, sodium N-cocoyl N-methyl taurid, and sodium lauryl methyl taurid); phosphate ester salts (sodium POE-oleyl ether phosphate, POE-stearyl ether phosphoric acid, etc.); sulfosuccinates (for example, sodium di-2-ethylhexylsulfosuccinate, sodium mono lauroyl mono ethanol amide polyoxyethylene sulfosuccinate, and sodium lauryl polypropylene glycol sulfosuccinate); alkylbenzene sulfonates (for example, sodium linear dodecylbenzenesulfonate, triethanolamine linear dodecylbenzenesulfonate, and linear dodecylbenzenesulfonic acid); higher fatty acid ester sulfates (for example, hydrogenated coconut oil aliphatic acid glycerin sodium sulfate); N-acyl glutamates (for example, mono sodium N-lauroylglutamate, disodium N-stearoylglutamate, and monosodium N-myristoyl-L-glutamate); sulfated oils (for example, turkey red oil); POE-alkyl ether carboxylic acid; POE-alkylaryl ether carboxylate; α-olefin sulfonate; higher fatty acid ester sulfonates; sec-alcohol sulfates; higher fatty acid alkyl amide sulfates; sodium lauroyl monoethanolamine succinates; ditriethanolamine N-palmitoylaspartate; and sodium case mate.

Examples of the cationic surfactants include alkyltrimethylammonium salts (for example, stearyltrimethylammonium chloride and lauryltrimethyl ammonium chloride) alkylpyridinium salts (for example, cetylpyridinium chloride), distearyldimethylammonium chloride dialkyldimethylammonium salt; poly(N,N'-dimethyl-3,5-methylene piperidinium) chloride; alkyl quaternary ammonium salts; alkyl dimethylbenzyl ammonium salts; alkyl isoquinolinium salts; dialkylmorpholine salts; POE alkyl amines; alkyl amine salts; polyamine fatty acid derivatives; amylalcohol fatty acid derivatives; benzalkonium chloride; and benzethonium chloride.

Examples of the ampholytic surfactants include: imidazoline type ampholytic surfactants (for example, 2-undecyl-N,N,N-(hydroxyethyl carboxymethyl)-2-imidazoline sodium salt and 2-coco yl-2-imidazolinium hydroxide-1-carboxyethyloxy 2 sodium salt); and betaine type surtactants (for example, 2-heptadecyl-n-carboxymethyl-n-hydroxyethyl imidazolinium betaine, lauryldimethylaminoacetic acid betaine, alkyl betaine, amide betaine, and sulfobetaine).

Examples of the lipophilic nonionic surface active agent include sorbitan fatty acid esters (for example, sorbitan monooleate, sorbitan monoisostearate, sorbitan mono laurate, sorbitan monopalmitate, sorbitan monostearate, sorbitan sesquioleate, sorbitan trioleate, diglycerol sorbitan penta-2-ethylhexylate, diglycerol sorbitan tetra-2-ethylhexylate); glycerin polyglycerin aliphatic acids (for example, mono-cottonseed oil fatty acid glycerin, glyceryl monoerucate, glycerin sesquioleate, glyceryl monostearate, α,α'-glyceryl oleate pyroglutamate, and glyceryl mono stearate malate);

propylene glycol fatty acid esters (for example, propylene glycol monostearate); hydrogenated castor oil derivatives; and glycerin alkylethers.

Examples of the hydrophilic nonionic surface active agents include: POE-sorbitan fatty acid esters (for example, POE-sorbitan monooleate, POE-sorbitan monostearate, POE-sorbitan monoolate, and POE-sorbitan tetraoleate); POE sorbitol fatty acid esters (for example, POE sorbitol monolaurate, POE-sorbitol monooleate, POE-sorbitol pentaoleate, and POE-sorbitol monostearate); POE-glycerin fatty acid esters (for example, POE-monooleates such as POE-glycerin monostearate, POE-glycerin monoisostearate, and POE-glycerin triisostearate); POE-fatty acid esters (for example, POE-distearate, POE-monodioleate, and ethylene glycol distearate); POE-alkylethers (for example, POE-lauryl ether, POE-oleyl ether, POE-stearyl ether, POE-behenyl ether, POE-2-octyl dodecyl ether, and POE-cholestanol ether); POE/POP-alkylethers (for example, POE/POP-cetyl ether, POE/POP-2-decyl tetradecyl ether, POE/POP-monobutyl ether, POE/POP-lanolin hydrate, and POE/POP-glycerin ether); POE-castor oil hydrogenated castor oil derivatives (for example, POE-castor oil, POE-hydrogenated castor oil, POE-hydrogenated castor oil monoisostearate, POE-hydrogenated castor oil triisostearate, POE-hydrogenated castor oil monopyroglutamic monoisostearic diester, and POE-hydrogenated castor oil maleic acid); POE-beeswax/lanolin derivatives (for example, POE-sorbitol beeswax); alkanol amides (for example, coconut fatty acid diethanol amide, lauric acid monoethanol amide, and aliphatic acid isopropanol amide); POE-propylene glycol fatty acid esters; POE-alkyl amine; POE-fatty acid amide; sucrose fatty acid ester; alkyl ethoxy dimethylamine oxides; and trioleyl phosphoric acid.

Examples of the humectant include polyethylene glycol, propylene glycol, glycerin, 1,3-butylene glycol, xylitol, sorbitol, maltitol, chondroitin sulfate, hyaluronic acid, mucoitin sulfuric acid, charonic acid, atelocollagen, cholesteryl-12-hydroxy stearate, sodium lactate, bile salt, dl-pyrrolidone carboxylic acid salt, short chain soluble collagen, diglycerin (EO)PO adduct, chestnut rose fruit extract, yarrow extract, and sweet clover extract.

Examples of the natural water-soluble polymer include: plant-type polymers (for example, gum arabic, gum tragacanth, galactan, guar gum, carob gum, karaya gum, carrageenan, pectin, agar, quince seed (*Cydonia oblonga*), algae colloids (brown algae extract), starches (rice, corn, potato, and wheat), and glycyrrhizic acid); microorganism-type polymers (for example, xanthan gum, dextran, succinoglucan, and pullulan); and animal-type polymers (for example, collagen, casein, albumin, and gelatin).

Examples of the semisynthetic water-soluble polymers include: starch-type polymers (for example, carboxymethyl starch and methylhydroxypropyl starch); cellulosic polymers (for example, methyl cellulose, ethyl cellulose, methylhydroxypropyl cellulose, hydroxyethyl cellulose, cellulose sodium sulfate, hydroxypropyl cellulose, carboxymetyl-cellulose, sodium carboxymethyl cellulose, crystal cellulose, and cellulose powder); and alginic acid-type polymers (for example, sodium alginate and propyleneglycol alginate).

Examples of the synthetic water-soluble polymers include: vinyl polymers (for example, polyvinyl alcohol, polyvinyl methyl ether, polyvinylpyrrolidone, carboxy vinyl polymer); polyoxyethylene-type polymers (for example, a copolymer of polyethylene glycol 20,000, 40,000, or 60,000 and polyoxyethylene polyoxypropylene); acrylic polymers (for example, sodium polyacrylate, polyethylacrylate, and polyacrylamide); polyethyleneimine; and cationic polymers.

Examples of the thickeners include: gum arabic, carrageenan, karaya gum, gum tragacanth, carob gum, quince seed (*Cydonia oblonga*), casein, dextrin, gelatin, sodium pectate, sodium arginate, methyl cellulose, ethyl cellulose, CMC, hydroxy ethyl cellulose, hydroxypropyl cellulose, PVA, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate (beagum), laponite, and silicic acid anhydride.

Examples of the sequestering agents include: 1-hydroxy ethane-1,1-diphosphonic acid, 1-hydroxy ethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, and trisodium ethylenediaminehydroxyethyl triacetate.

Examples of the lower alcohols include ethanol, propanol, isopropanol, isobutyl alcohol, and t-butyl alcohol.

Examples of the polyhydric alcohols include: dihydric alcohols (for example, ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (for example, glycerin and trimethylolpropane); tetrahydric alcohols (for example, pentaerythritols such as 1,2,6-hexanetriol); pentahydric alcohols (for example, xylitol); hexahydric alcohols (for example, sorbitol, mannitol); polyhydric alcohol polymers (for example, diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkylethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono 2-methyl hexyl ether, ethylene glycol isoamyl ether, ethylene glycol benzyl ether, ethylene glycol isopropyl ether, ethylene glycol dimethylether, ethylene glycol diethyl ether, and ethylene glycol dibutyl ether); dihydric alcohol ether esters (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycolmonomethyl ether acetate, propylene glycol monoethyl ether acetate, propylene glycol monopropyl ether acetate, and propylene glycol monophenyl ether acetate); glycerin mono alkyl ethers (for example, xylyl alcohol, selachyl alcohol, and batyl alcohol); sugar alcohols (for example, sorbitol, maltitol, maltotriose, mannitol, sucrose, erythritol, glucose, fructose, starch amylolysis sugar, maltose, xylitose, and alcohol prepared by the reduction of starch amylolysis sugar); glysolid; tetrahydro furfuryl alcohol; POE-tetrahydro furfuryl alcohol; POP-butyl ether; POP/POE-butyl ether; tripolyoxypropylene glycerin ether; POP-glycerin ether, POP-glycerin ether phosphoric acid; POP/POE-pentane erythritol ether, and polyglycerin.

Examples of the monosaccharides include: trioses (for example, D-glyceryl aldehyde and dihydroxyacetone); tetroses (for example, D-etythrose, D-erythrulose, D-threose, and erythritol); pentoses (for example, L-arabinose, D-xylose, L-lyxose, D-arabinose, D-ribose, D-ribulose, D-xylulose, and L-xylulose); hexoses (for example, D-glucose, D-talose, D-psicose, D-galactose, D-fructose, L-galactose, L-mannose, and D-tagatose); heptoses (for example, aldoheptose and heprose); octoses (for example, octurose);

deoxysugars (for example, 2-deoxy-D-ribose, 6-deoxy-L-galactose, and 6-deoxy-L-mannose); amino sugars (for example, D-glucosamine, D-galactosamine, sialic acid, amino uronic acid, and muramic acid); and uronic acid (for example, D-glucuronic acid, D-mannuronic acid, L-guluronic acid, D-galacturonic acid, and L-iduronic acid).

Examples of the oligosaccharides include sucrose, umbelliferose, lactose, planteose, isolignoses, α,α-trehalose, raffinose, lignoses, umbilicine, stachyose and verbascose.

Examples of the polysaccharides include cellulose, quince seed, chondroitin sulfate, starch, galactan, dermatan sulfate, glycogen, gum arabic, heparan sulfate, hyaluronic acid, traganth gum, keratan sulfate, chondroitin, xanthan gum, mucoitin sulfuric acid, guar gum, dextran, kerato sulfate, locustbean gum, succinoglucane, and charonic acid.

Examples of the amino acids include neutral amino acids (for example, threonine and cysteine) and basic amino acids (for example, hydroxylysine). Examples of the amino acid derivatives include sodium acyl sarcosinate (sodium N-lauroyl sarcosinate), acyl glutamate, sodium acyl β-alanine, glutathione, and pyrrolidone carboxylic acid.

Examples of the organic amines include monoethanolamine, diethanolamine, triethanolamine, morpholine, triisopropanolamine, 2-amino-2-methyl-1,3-propanediol, and 2-amino-2-methyl-1-propanol.

Examples of the high polymer emulsions include acrylic resin emulsions, ethyl polyacrylate emulsions, acryl resin liquids, polyacrylic alkyl ester emulsions, polyvinyl acetate resin emulsions, and natural rubber latex.

Examples of the pH adjustment agents include buffers such as lactic acid-sodium lactate, citric acid-sodium citrate, and succinic acid-sodium succinate.

Examples of the vitamins include vitamins A, B1, B2, B6, C and E as well as their derivatives, pantothenic acid and its derivatives, and biotin.

Examples of the antioxidants include tocopherols, dibutyl hydroxytoluene, butyl hydroxyanisole, and gallic ester.

Examples of the antioxidation auxiliary agents include phosphoric acid, citric acid, ascorbic acid, maleic acid, malonic acid, succinic acid, fumaric acid, cephalin, hexameta phosphate, phytic acid, and ethylene diamine tetraacetic acid.

Examples of other possible ingredients include antiseptics (ethylparaben, butylparaben, etc.); anti-inflammatory agents (for example, glycyrrhizic acid derivatives, glycyrrhetinic acid derivatives, salicylic acid derivatives, hinokitiol, zinc oxide, and allantoin); whitening agents (for example, placenta extract, creeping saxifrage extract and arbutin); various extracts (for example, Phellodendri Cortex, goldthread, lithospermum root, *Paeonia lactiflora, Swertia japonica*, Birch, sage, loquat, carrot, aloe, Malva sylvestris, Iris, grape, *Coix* ma-yuen, sponge gourd, lily, saffron, *Cnidium officinale*, sheng jiang, *Hypericum erectum*, Ononis, garlic, Guinea pepper, chen pi, *Ligusticum acutilobum*, and seaweed), activators (royal jelly, photosensitive substances, and cholesterol derivatives); blood circulation promoting agents (for example, nonyl acid valenyl amide, nicotinic acid benzyl esters, nicotinic acid β-butoxy ethyl esters, capsaicin, gingeron, cantharis tincture, Ichthammol, tannic acid, α-borneol, tocopherol nicotinate, inositol hexanicotinate, cyclandelate, cinnarizine, tolazoline, acetylcholine, verapamil, cepharanthine, and ã-orizanol); anti-seborrhea agents (for example, sulfur and thiantol); and antiinflammatory agents (for example, tranexamic acid, thiotaurine, and hypotaurine).

Ultraviolet absorbents and drugs can be blended into the skin treatment composition of the present invention in a stable manner. Therefore, it is preferable to blend in slightly soluble ultraviolet absorbents or slightly soluble drugs that are hard to be blend stably in a conventional oil component due to poor solubility.

Examples of the ultraviolet absorbents preferably blended into the skin treatment composition of the present invention include triazine-type ultraviolet absorbents which do not dissolve easily in conventional oil components. For example, an ultraviolet absorbent such as bisresorsinyl triazine is preferably blended in. More specifically, 2,4-bis{[4-(2-ethylhexyloxy)-2-hydroxy]phenyl}-6-(4-methoxyphenyl)1,3,5-triazine and 2,4,6-tris{4-(2-ethylhexyloxycarbonyl)anilino}1,3,5-triazine, used by the name of octyl triazone are preferably blended in.

Any formulation can be used including the solution type, the solubilized type, emulsion type, powder dispersion type, water-oil bilayer type, and water-oil-powder three layer type. The product form of the skin treatment composition of the present invention is arbitrary. It can be used in lotions, emulsions, creams, facial cosmetics such as packs, makeup cosmetics such as foundations, lipsticks, and eye shadows, body cosmetics, aroma cosmetics, cleaners, and ointments.

For blending in ultraviolet absorbents and/or drugs, emulsions and cream-like emulsified compositions are preferable from the point of view of usability.

[Invention Defined in Claims 3-7]

The compound of general formula (2) is an ester bond product of polyhydroxystearic acid prepared by the ester polymerization of polyethylene glycol and hydroxystearic acid; it acts as an emulsifier in the present invention.

Preferable specific examples of general formula (2) are those for which m is 10-100, more preferably 20-60, and a+b is 3-20, more preferably 5-15.

The compound of general formula (3) is an ester bond product of polyhydroxystearic acid prepared by the ester polymerization of polyglycerin and hydroxystearic acid; it acts as an emulsifier in the present invention.

Preferable specific examples of general formula (3) are those for which n is 1-30, more preferably 3-10, and a+b is 3-20, more preferably 5-15. Specific compounds that can be used preferably are decaglycerin pentaisostearate and tetraglycerin pentastearate.

In the compounds of general formulas (2) and (3), $R^1$ and $R^2$, independently of each other, denote a hydrogen atom or a lower alkyl group having 1-6 carbon atoms.

Examples of the lower alkyl group having 1-6 carbon atoms include both straight chains and branched chains such as a methyl group, ethyl group, propyl group, isopropyl group, butyl group, sec-butyl group, tert-butyl group, pentyl group, isopentyl group, neopentyl group, tert-pentyl group, and hexyl group.

A specific example of the compound of general formula (2) is commercially available as Aracel P135 (from ICI Surfactants).

Also, a specific example of the compound of general formula (3) is commercially available as Dehymuls PGPH (from CognisDeutschland GmbH), which is polyglyceryl-2 dipolyhydroxyhisstearate for which $R^1$ and $R^2$ are both hydrogen atoms.

In the present invention, one, two or more of the compounds that satisfy the aforementioned general formula (2) are used for the emulsifier. In the sunblock water-in-oil type emulsified cosmetic of the present invention, the compound of general formula (2) manifests an exceptional emulsifying ability and thus is capable of providing a sunblock cosmetic with superior emulsification stability. Since a sunblock cosmetic can be left unattended under severe summer conditions, the exceptional emulsification stability manifested by the present invention is a very useful effect.

The blend ratio of the compound that satisfies general formula (2) is preferably 0.1-5.0% (mass percentage), more preferably 0.5-2.0%, of the water-in-oil type emulsified composition. If it is less than 0.1%, then the oil phase portion in which the ultraviolet absorbent is dissolved cannot be emulsified stably for a long time; if it is more than 5.0%, then spreading on the skin tends to become poor. Because of the superior emulsifying ability, a blend ratio of 0.5-2.0% (mass percentage) can provide a sunblock cosmetic that has superior emulsification stability and no problem in terms of spreading on the skin.

Also, one, two or more of the compounds that satisfy the aforementioned general formula (3) are used for the emulsifier. In the sunblock water-in-oil type emulsified cosmetic of the present invention, introduction of the compound of general formula (3) makes it possible to provide a sunblock cosmetic that is particularly superior in terms of spreading on the skin. Since a sunblock cosmetic is spread all over the skin, the use of the compound of general formula (3) as an emulsifier in the present invention results in a sunblock cosmetic that is superior in terms of the ultraviolet prevention effect on the entire skin due to good spreadability that allows homogeneous application on the entire skin and helps prevent missed areas.

The blend ratio of the compound that satisfies general formula (3) is preferably 0.1-5.0% (mass percentage), more preferably 0.5-4.0%, of the water-in-oil type emulsified composition. If it is less than 0.1%, then the oil phase portion in which the ultraviolet absorbent is dissolved cannot be emulsified stably for a long period; if it is more than 5.0%, then stickiness may arise.

Furthermore, in the present invention, joint use of one, two or more of the compounds that satisfy general formula (2) and one, two or more of the compounds that satisfy the aforementioned general formula (3) is particularly preferable in view of superior emulsification stability and spreadability.

When the compound that satisfies general formula (2) and the compound that satisfies general formula (3) are used jointly, the total blend ratio of the two is preferably 0.1-5.0% (mass percentage). If it is less than 0.1%, then the oil phase portion in which the ultraviolet absorbent is dissolved cannot be emulsified stably for a long period; if it is more than 5.0%, then stickiness and/or poor spreadability may result.

The relative blend ratio of the compound of general formula (2) and the compound of general formula (3) is determined according to the recipe of the sunblock cosmetic; a preferable mass ratio is Compound of general formula (2):Compound of general formula (3)=1:1 to 1:2. For the blend ratio of each compound, the blend ratio of the compound of general formula (2) is preferably 0.5-1.5% (mass percentage) and the blend ratio of the compound of general formula (3) is preferably 0.5-2.0% (mass percentage).

Emulsifiers other than those described above can also be added within the range that does not spoil the effects of the present invention; however, there is no substantial need for such addition.

The alkyl benzoate having a specific structure that is used as an oil component to dissolve the ultraviolet absorbent is described below.

The alkyl benzoate used in the present invention is represented by the aforementioned general formula (1). In general formula (1), R denotes a branched or straight chain alkyl group having 8-15 carbon atoms. Alkyl groups having six or less carbon atoms are volatile and also problematic due to the odor; alkyl groups having 16 or more carbon atoms spoil the refreshing sensation at the time of application. Preferable are straight chain or branched alkyl groups having 8-10 carbon atoms, more preferable is a 3,7-dimethyloctane group, for which R has 10 carbon atoms.

Preferable examples of the alkyl benzoate of general formula (1) include octyl benzoate, 2-ethylhexyl benzoate, 3,5,5-trimethylhexyl benzoate, and 3,7-dimethyloctyl benzoate. Of these, 3,7-dimethyloctyl benzoate is particularly preferable in terms of the sensation at the time of application, solubility of the ultraviolet absorbent, and a lack of odor.

The alkyl benzoate of general formula (1) can be prepared by reacting an alcohol with an alkyl group having a target number of carbons and benzoyl chloride in the presence of triethylamine, using chloroform as the solvent; the reaction formula is shown below and the yield is 90% or higher.

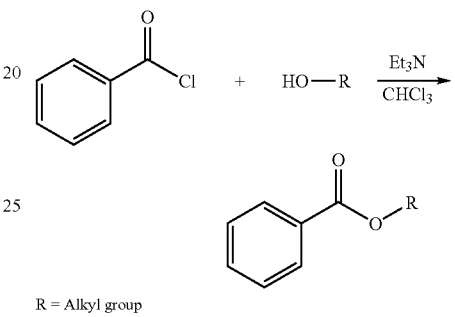

R = Alkyl group

Also, alkyl benzoates having 12-15 carbon atoms are commercially available as well. For example, Crodamol AB (from Croda, Inc.), which is a mixture of alkyl groups having 12-15 carbon atoms, are commercially available.

The blend ratio of the alkyl benzoate is not limited in particular; usually it is 0.1-50.0% (mass percentage), more preferably 0.5-30.0% (mass percentage), of the water-in-oil type emulsified composition. If it is less than 0.1%, then the effect of dissolving the ultraviolet absorbent is not manifested; if it is more than 50.0%, then a sticky sensation may result.

The following compounds are examples of the ultraviolet absorbent used in the present invention.

A: Triazine-type Ultraviolet Absorbents

For example, bisresorsinyl triazine.
More specifically, bis{[4-(2-ethylhexyloxy)-2-hydroxy]phenyl}-6-(4-methoxyphenyl)1,3,5-triazine, 2,4,6-tris{4-(2-ethylhexyloxycarbonyl)anilino}1,3,5-triazine, etc.

B: Benzoic Acid-type Ultraviolet Absorbents

For example, p-aminobenzoic acid (hereafter abbreviated as PABA), PABA monoglycerin ester, N, N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester.

C: Anthranilic Acid-type Ultraviolet Absorbents

For example, homo mentyl-N-acetyl anthranilate.

D: Salicylic Acid-type Ultraviolet Absorbents

For example, amyl salicylate, mentyl salicylate, homo mentyl salicylate, octyl salicylate, phenyl salicylate, benzyl salicylate, and p-isopropanol phenyl salicylate.

E: Cinnamic Acid-type Ultraviolet Absorbents

For example, octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethyl hexanoyl-di-p-methoxy cinnamate.

F: Other Ultraviolet Absorbents

For example, 3-(4'-methylbenzylidene)-d, 1-camphor, 3-benzylidene-d, 1-camphor, 2-phenyl-5-methyl benzoxazol, 2-(2'-hydroxy-5'-methylphenyl) benzotriazol, 2-(2'-hydroxy-5'-t-octylphenyl) benzotriazol, 2-(2'-hydroxy-5'-methylphenyl benzotriazol, dibenzaladine, dianisoylmethane, and 4-methoxy-4'-t-butyl dibenzoyl-methane, 5-(3,3-dimethyl-2-norbornylidene)-3-pentane-2-one.

It is particularly preferable to use a highly polar triazine-type ultraviolet absorbent, such as bisresorsinyl triazine. More specifically, 2,4-bis{[4-(2-ethylhexyloxy)-2-hydroxy]phenyl}-6-(4-methoxyphenyl)1,3,5-triazine and 2,4,6-tris{4-(2-ethylhexyloxycarbonyl)anilino}1,3,5-triazine, used by the name of octyl triazone are preferably blended in.

The blend ratio of the ultraviolet absorbent is not limited in particular, but usually 0.01-30.0% (ultraviolet absorbent) of the water-in-oil type emulsified composition is preferable. The blend ratio is determined based on the target ultraviolet absorption effect (SPF value).

Since the sunblock cosmetic of the present invention can dissolve slightly soluble highly polar ultraviolet absorbents that are difficult to introduce in a stable manner, a desired ultraviolet absorbent can be introduced at a desired blend ratio. Therefore, sunblock cosmetics that are superior in emulsification stability, have a high ultraviolet absorption effect and improved SPF value can be provided. Since even slightly soluble drugs can be dissolved in a stable manner, it is also preferable to introduce slightly soluble drugs according to the purpose.

In the present invention, it is preferable to further introduce an ultraviolet scattering agent (ultraviolet protection powder).

Examples of the ultraviolet scattering agent include the powders of titanium oxide, fine particle titanium oxide, zinc oxide, fine particle zinc oxide, iron oxide, fine particle iron oxide, and cerium oxide. The powder used is usually in the form of needles, cones, spheres and granules. Fine particle powder having a particle size of 0.1 micrometers or less is preferable.

Ultraviolet scattering agents prepared by hydrophobicizing these powders are also preferable. Examples include powders treated with silicone by using methylhydrogen polysiloxane, silane coupling agents and such, powders treated with metal soap, powders treated with fluoride by using diethanolamine perfluoroalkylphosphate, perfluoroalkylsilane and such, and powders treated with dextrin fatty acid ester.

The blend ratio of the ultraviolet scattering agent is not limited in particular. It is usually 0.5-50% (mass percentage), preferably 1-30% (mass percentage), of the total amount of the sunblock cosmetic. If the blend ratio is too high, it may not be preferable in terms of sensation at the time of application and stability.

In addition to the aforementioned essential ingredients, other ingredients used in skin treatment compositions can be blended in as necessary in the skin treatment composition of the present invention; examples of such ingredients include powder ingredients, liquid fats and oils, solid fats and oils, waxes, hydrocarbons, higher fatty acids, higher alcohols, esters, silicones, anionic surfactants, cationic surfactants, ampholytic surfactants, nonionic surfactants, humectants, water-soluble polymers, thickeners, coating agents, sequestering agents, lower alcohols, polyhydric alcohols, sugars, amino acids, organic amines, polymer emulsions, pH adjusting agents, skin nutrients, vitamins, antioxidants, antioxidation assistants, perfumes, and water; and the skin treatment composition can be prepared for the target formulation with a conventional method. Specific possible ingredients are the same as the aforementioned possible ingredients for the skin treatment composition. The aforementioned essential ingredients and any one, two or more of the aforementioned ingredients are blended in to prepare the sunblock cosmetic of the present invention.

The formulation of the sunblock cosmetic of the present invention is an water-in-oil type emulsified composition; preferable examples are emulsion and/or cream type sunblock cosmetics.

EXAMPLES

The present invention is described in detail below by referring to Examples. The present invention is not limited to these examples. First, synthesis examples of the alkyl benzoate used in the present invention are described.

Synthesis Example 1

3,7-dimethyloctyl benzoate (isodecyl benzoate)

Chloroform (300 mL) was put into an argon-substituted 2 L three-neck flask and benzoyl chloride (100 mL, 0.86 mol) was added, followed by stirring at room temperature. Subsequently, 3,7-dimethyloctanol (246 mL, 1.3 mol) was dripped in, and, after the temperature was lowered to 0° C. with ice, triethylamine (120 mL, 0.86 mL) was dripped in, and six hours of stirring was carried out as the temperature was gradually raised to room temperature. Unreacted benzoyl chloride was quenched by adding 100 mL of water, followed by rinsing with 200 mL of 0.1 N hydrochloric acid and drying with sodium sulfate; the solvent was then removed under reduced pressure. The obtained orange colored oil-like product was distilled under a reduced pressure of 0.5 mmHg to obtain a colorless, odorless oil-like compound (yield 82%). The structure was verified using $^{13}$C NMR; 3,7-dimethyloctyl benzoate with the following structural formula was obtained. FIG. 1 shows the $^{13}$C NMR spectrum. The IOB value of the obtained oil component is 0.23.

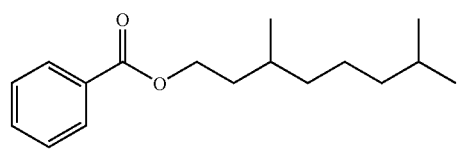

Synthesis Example 2

3,5,5-trimethylhexyl benzoate (isononyl benzoate)

Figure 2:
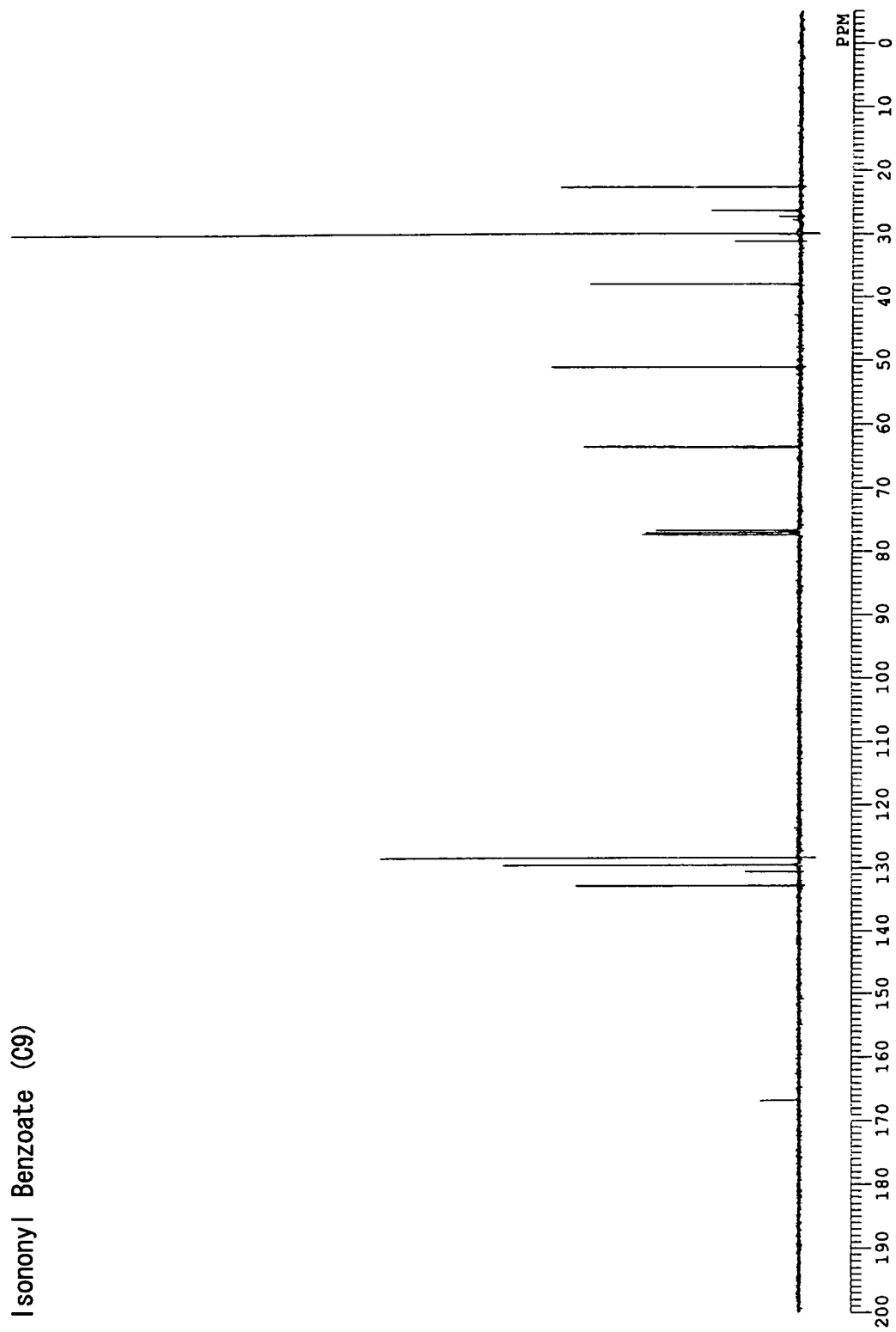
FIG. 2 shows a $^{13}$C NMR spectrum of synthesis example 2.

Chloroform (300 mL) was put into an argon-substituted 2 L three-neck flask and benzoyl chloride (100 mL, 0.86 mol) was added, followed by stirring at room temperature. Subsequently, 3,5,5-trimethyl-1-hexanol (225 mL, 1.3 mol) was dripped in, and, after the temperature was lowered to 0° C.

with ice, triethylamine (120 mL, 0.86 mL) was dripped in and six hours of stirring was carried out as the temperature was gradually raised to room temperature. Unreacted benzoyl chloride was quenched by adding 100 mL of water, followed by rinsing with 200 mL of 0.1 N hydrochloric acid and drying with sodium sulfate; the solvent was then removed under reduced pressure. The obtained orange colored oil-like product was distilled under a reduced pressure of 0.5 mmHg to obtain a colorless oil-like compound (yield 85%). The structure was verified using $^{13}$C NMR; 3,5,5-trimethylhexyl benzoate with the following structural formula was obtained. FIG. 2 shows the $^{13}$C NMR spectrum. The IOB value of the obtained oil component is 0.26.

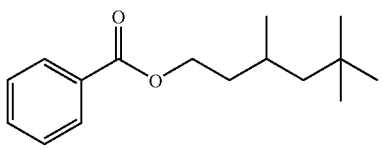

Synthesis Example 3

2-ethylhexyl benzoate

Figure 3:
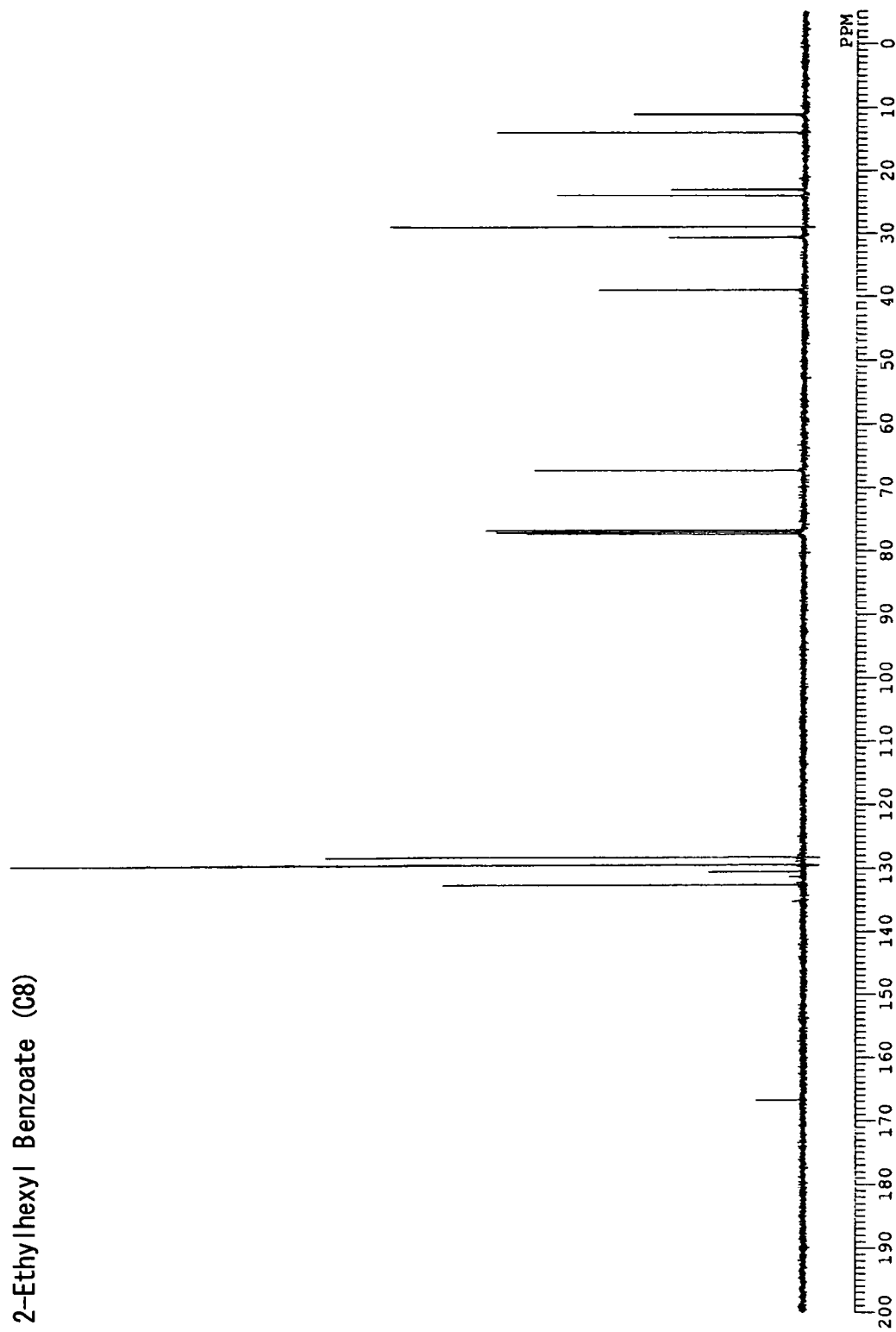
FIG. 3 shows a $^{13}$C NMR spectrum of synthesis example 3.

Chloroform (300 mL) was put into an argon-substituted 2 L three-neck flask and benzoyl chloride (100 mL, 0.86 mol) was added, followed by stirring at room temperature. Furthermore, 2-ethyl-1-hexanol (202 mL, 1.3 mol) was dripped in, and, after the temperature was lowered to 0° C. with ice, triethylamine (120 mL, 0.86 mL) was dripped in and six hours of stirring was carried out as the temperature was gradually raised to room temperature. Unreacted benzoyl chloride was quenched by adding 100 mL of water, followed by rinsing with 200 mL of 0.1 N hydrochloric acid and drying with sodium sulfate; the solvent was then removed under reduced pressure. The obtained orange colored oil-like product was distilled under a reduced pressure of 0.5 mmHg to obtain a colorless oil-like compound (yield 83%). The structure was verified using $^{13}$C NMR; 2-ethylhexyl benzoate with the following structural formula was obtained. FIG. 3 shows the $^{13}$C NMR spectrum. The IOB value of the obtained oil component is 0.26.

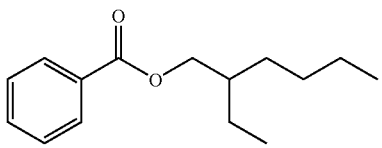

[Examples of the Sunblock Cosmetics of Claim 1 and Claim 2]

The alkyl benzoates obtained in the aforementioned synthetic examples 1-3 were added to a skin treatment composition and evaluated. The blend ratios are in % (mass-percentage) units unless specified otherwise.

The testing method and the evaluation method are described first.

"Evaluation (1): Refreshing Sensation on the Skin"

The refreshing sensation on the skin during use was evaluated with actual use testing by ten specialized panelists. The evaluation criteria are as follows:

⊚ . . . Eight or more specialized panelists reported a refreshing sensation on the skin during use.
◯ . . . Six or more and less than eight specialized panelists reported a refreshing sensation on the skin during use.
Δ . . . Three or more and less than six specialized panelists reported a refreshing sensation on the skin during use.
X . . . Less than three specialized panelists reported a refreshing sensation on the skin during use.

"Evaluation (2): Non-stickiness on the Skin"

The non-stickiness on the skin during use was evaluated with actual use testing by ten specialized panelists. The evaluation criteria are as follows:

⊚ . . . Eight or more specialized panelists reported non-stickiness on the skin during use.
◯ Six or more and less than eight specialized panelists reported non-stickiness on the skin during use.
Δ . . . Three or more and less than six specialized panelists reported non-stickiness on the skin during use.
X . . . Less than three specialized panelists reported non-stickiness on the skin during use.

"Evaluation (3): Solubility of the Ultraviolet Absorbent"

A solubility test of a slightly soluble ultraviolet absorbent (triazine derivative) at a low temperature (0° C.) was carried out.

Examples 1-1 to 1-8, Comparative Examples 1-1 to 1-3

Skin treatment compositions (O/W type emulsion) consisting of the blend composition described in Table 1-1, Table 1-2, and Table 1-3 were prepared with a conventional method and the aforementioned evaluation test was conducted. The results are shown in the tables. The evaluation test results for the aforementioned evaluation (3) are shown in Table 1-4.

TABLE 1-1

| | Examples | | | |
|---|---|---|---|---|
| Ingredients | 1-1 | 1-2 | 1-3 | 1-4 |
| 3,7-dimethyloctyl benzoate | 0.001 | 0.1 | 1.0 | 5.0 |
| Sodium hexamethaphosphate | 0.01 | 0.01 | 0.01 | 0.01 |
| Trisodium edetate | 0.03 | 0.03 | 0.03 | 0.03 |
| 1,3-butylene glycol | 5 | 5 | 5 | 5 |
| Potassium hydroxide | 0.1 | 0.1 | 0.1 | 0.1 |
| Carboxyvinyl polymer | 0.1 | 0.1 | 0.1 | 0.1 |
| Preservative | 0.15 | 0.15 | 0.15 | 0.15 |
| Purified water | Balance | Balance | Balance | Balance |
| Evaluation (1): Refreshing sensation on the skin | ◯ | ⊚ | ⊚ | ⊚ |
| Evaluation (2): Non-stickiness on the skin | ◯ | ⊚ | ⊚ | ⊚ |

TABLE 1-2

| | Examples | | |
|---|---|---|---|
| Ingredients | 1-5 | 1-6 | 1-7 |
| 2-ethylhexyl benzoate | 5 | — | — |
| 3,5,5-trimethylhexyl benzoate | — | 5 | — |
| 3,7-dimethyloctyl benzoate | — | — | 5 |
| Sodium hexamethaphosphate | 0.01 | 0.01 | 0.01 |
| Trisodium edetate | 0.03 | 0.03 | 0.03 |
| 1,3-butylene glycol | 5 | 5 | 5 |
| Potassium hydroxide | 0.1 | 0.1 | 0.1 |
| Carboxyvinyl polymer | 0.1 | 0.1 | 0.1 |

TABLE 1-2-continued

| Ingredients | Examples | | |
|---|---|---|---|
| | 1-5 | 1-6 | 1-7 |
| Preservative | 0.15 | 0.15 | 0.15 |
| Purified water | Balance | Balance | Balance |
| Evaluation (1): Refreshing sensation on the skin | ◎ | ◎ | ◎ |
| Evaluation (2): Non-stickiness on the skin | ◎ | ◎ | ◎ |

TABLE 1-3

| Ingredients | Example | Comparative examples | | |
|---|---|---|---|---|
| | 1-8 | 1-1 | 1-2 | 1-3 |
| 3,7-dimethyloctyl benzoate | 5 | — | — | — |
| Decamethyl cyclopentane siloxane | — | 5 | — | — |
| Isocetyl oleate | — | — | 5 | — |
| Liquid petrolatum | — | — | — | 5 |
| Sodium hexamethaphosphate | 0.01 | 0.01 | 0.01 | 0.01 |
| Trisodium edetate | 0.03 | 0.03 | 0.03 | 0.03 |
| 1,3-butylene glycol | 5 | 5 | 5 | 5 |
| Potassium hydroxide | 0.1 | 0.1 | 0.1 | 0.1 |
| Carboxyvinyl polymer | 0.1 | 0.1 | 0.1 | 0.1 |
| Preservative | 0.15 | 0.15 | 0.15 | 0.15 |
| Purified water | Balance | Balance | Balance | Balance |
| Evaluation (1): Refreshing sensation on the skin | ◎ | ◎ | ◎ | ○ |
| Evaluation (2): Non-stickiness on the skin | ◎ | ◎ | ◎ | ◎ |

The solubility of a slightly soluble ultraviolet absorbent in the alkyl benzoate obtained in synthetic examples 1-3 was measured. For the slightly soluble ultraviolet absorbent, a triazine-type ultraviolet absorbent 2,4-bis{[4-(2-ethylhexyloxy)-2-hydroxy]phenyl}-6-(4-methoxyphenyl)1,3,5-triazine was used.

The solubility is expressed as a concentration (mass percentage) in a saturated solution at 0° C.

For the alkyl benzoate having 12-15 carbon atoms, a commercial product (Crodamol AB from Croda, Inc.) was used. This oil component is a mixture of alkyl benzoates having 12-15 carbon atoms.

The alkyl benzoate used in the skin treatment composition of the present invention is shown to have a distinctively increased ability to dissolve slightly soluble drugs, compared with alkyl benzoates having 12-15 carbon atoms and other oil components.

Furthermore, 3,7-dimethyloctyl benzoate turned out to be an excellent oil component without any odor.

TABLE 1-4

| Oil components | Solubility |
|---|---|
| 2-ethylhexyl benzoate (Carbon number 8) | 12% |
| 3,5,5-trimethylhexyl benzoate (Carbon number 9) | 13% |
| 3,7-dimethyloctyl benzoate (Carbon number 10) | 12% |
| Alkyl benzoate (Carbon number 12–15) | 8% |
| Di-2-ethylhexyl succinate | 4% |
| Pentaerythrite tetra (2-ethylhexanoate/paramethoxycinnamate) | 4% |

TABLE 1-4-continued

| Oil components | Solubility |
|---|---|
| Decamethyl cyclopentane siloxane | 0% |
| Liquid petrolatum | 0% |

The results above show that the skin treatment compositions of the present invention exhibit superior effects for all the evaluation items. That is, as an oil component to be added to a skin treatment composition, the specific alkyl benzoates used in the present invention are comparably excellent in terms of giving a refreshing sensation and no stickiness, compared with conventional oil components. Furthermore, since the ability to dissolve slightly soluble ultraviolet absorbents is also high, a skin treatment composition with a desired blend ratio of slightly soluble ultraviolet absorbents or drugs can be provided. In particular, the alkyl benzoates having 10 carbon atoms are odorless and function as an excellent oil component for a skin treatment composition.

Other Examples of the skin treatment composition of the present invention are shown below.

Example 1-9 Sunblock Emulsion

A. Oil Phase

| | |
|---|---|
| Volatile cyclic silicone (Decamethyl cyclopentane siloxane) | 27.0% |
| Silicone-hydrophobicized titanium dioxide | 10.0 |
| Silicone-hydrophobicized zinc oxide | 10.0 |
| Silicone-hydrophobicized talc | 4.0 |
| 3,7-dimethyloctyl benzoate (synthetic example 1) | 10.0 |
| Octylmethoxy cinnamate | 5.0 |
| 4-methoxy-4'-t-butyl dibenzoyl-methane | 2.0 |
| 2,4-bis{[4-(2-ethylhexyloxy)-2-hydroxy]phenyl}-6-(4-methoxyphenyl)1,3,5-triazine | 3.0 |
| Organically modified montmorillonite | 0.5 |
| Preservative | Appropriate amount |
| Perfume | Appropriate amount |

(Preparation Method and Evaluation)

The oil phase and the water phase are each mixed and dissolved. Dispersion of titanium dioxide in the oil phase portion is thoroughly conducted, to which the water phase portion is added, and emulsification is carried out using a homogenizer. The obtained sunblock emulsion is superior in terms of a refreshing sensation. It is also superior in terms of stable dissolution of the slightly soluble ultraviolet absorbent 2,4-bis{[4-(2-ethylhexyloxy)-2-hydroxy]phenyl}-6-(4-methoxyphenyl)1,3,5-triazine.

Example 1-10 Sunblock Cream

A. Oil Phase

| | |
|---|---|
| Stearic acid | 10.0% |
| Stearyl alcohol | 4.0 |
| Butyl stearate | 8.0 |
| Monoglycerin stearate | 2.0 |
| Vitamin E acetate | 0.5 |
| Vitamin A palmitate | 0.1 |
| 3,7-dimethyloctyl benzoate (synthetic example 1) | 10.0 |

-continued

| | |
|---|---|
| 2,4-bis{[4-(2-ethylhexyloxy)-2-hydroxy]phenyl}-6-(4-methoxyphenyl) 1,3,5-triazine | 3.0 |
| Macadamia nut oil | 1.0 |
| Tea seed oil | 3.0 |
| Perfume | 0.4 |
| Preservative | Appropriate amount |

B. Water Phase

| | |
|---|---|
| Glycerin | 4.0 |
| 1,2 pentane diol | 3.0 |
| Sodium hyaluronate | 1.0 |
| Potassium hydroxide | 2.0 |
| Magnesium ascorbate phosphate | 0.1 |
| L-arginine hydrochloride | 0.01 |
| Trisodium edetate | 0.05 |
| Purified water | Balance |

(Preparation Method and Evaluation)

Oil phase A and water phase B are each heated up to 70° C. to be dissolved completely. The A phase is added to the B phase, followed by emulsification by means of an emulsifier. The emulsion is cooled by a heat exchanger to obtain a cream. The obtained cleansing oil exhibits superior smoothness, no stickiness, and sustained moisture retention. It is also superior in terms of stable dissolution of the slightly soluble ultraviolet absorbent 2,4-bis{[4-(2-ethylhexyloxy)-2-hydroxy]phenyl}-6-(4-methoxyphenyl)1,3,5-triazine.

Example 1-11 Cream

A. Oil Phase

| | |
|---|---|
| Cetanol | 4.0% |
| Petrolatum | 7.0 |
| Isopropyl myristate | 8.0 |
| Squalane | 10.0 |
| 3,7-dimethyloctyl benzoate (synthetic example 1) | 10.0 |
| 2,4-bis{[4-(2-ethylhexyloxy)-2-hydroxy]phenyl}-6-(4-methoxyphenyl) 1,3,5-triazine | 3.0 |
| Monoglycerin stearate | 2.2 |
| POE(20) sorbitan monostearate | 2.8 |
| 3,7-dimethyloctyl benzoate (synthetic example 1) | 20.0 |
| Vitamin E nicotinate | 2.0 |
| Perfume | 0.3 |
| Antioxidant | Appropriate amount |
| Preservative | Appropriate amount |

B. Water Phase

| | |
|---|---|
| Glycerin | 10.0 |
| Sodium hyaluronate | 0.02 |
| Dipropylene glycol | 4.0 |
| Sodium pyrrolidone carboxylate | 1.0 |
| Disodium edetate | 0.01 |
| Purified water | Balance |

(Preparation Method and Evaluation)

Oil phase A and water phase B are each heated up to 70° C. to be dissolved completely. The A phase is added to the B phase, followed by emulsification by means of an emulsifier. The emulsion is cooled by a heat exchanger to obtain a cream. The obtained cream exhibits superior smoothness, no stickiness, and sustained moisture retention. It is also superior in terms of stable dissolution of the slightly soluble ultraviolet absorbent 2,4-bis{[4-(2-ethylhexyloxy)-2-hydroxy]phenyl}-6-(4-methoxyphenyl)1,3,5-triazine.

Example 1-12 Foundation

A. Oil Phase

| | |
|---|---|
| Cetanol | 3.5% |
| Deodorized lanolin | 4.0 |
| Jojoba oil | 5.0 |
| Petrolatum | 2.0 |
| Squalane | 6.0 |
| Monoglycerin stearate | 2.5 |
| POE(60) hydrogenated castor oil | 1.5 |
| POE(20) cetyl ether | 1.0 |
| 3,7-dimethyloctyl benzoate (synthetic example 1) | 2.0 |
| Pyridoxine tripalmitate | 0.1 |
| Preservative | Appropriate amount |
| Perfume | 0.3 |

B. Water Phase

| | |
|---|---|
| Propylene glycol | 10.0 |
| Powder preparation | 12.0 |
| Trisodium ethylenediaminehydroxyethyl triacetate | 1.0 |
| Purified water | Balance |

(Preparation Method and Evaluation)

Oil phase A and water phase B are each heated up to 70° C. to be dissolved completely. The A phase is added to the B phase, followed by emulsification by means of an emulsifier. The emulsion is cooled by a heat exchanger to obtain an emulsified foundation. This emulsified foundation is a cream that exhibits superior smoothness, no stickiness, superior refreshing sensation, and sustained moisture retention. It is also superior in terms of stable dissolution of the slightly soluble ultraviolet absorbent 2,4-bis{[4-(2-ethylhexyloxy)-2-hydroxy]phenyl}-6-(4-methoxyphenyl)1,3,5-triazine.

Example 1-13 W/O Sunblock (Cream)

Ingredients

| Material | Blend ratio (mass percentage) |
|---|---|
| Water | |
| Ion-exchanged water | Balance |
| Humectant | |
| 1,3-butylene glycol | 5.0 |

-continued

| Material | Blend ratio (mass percentage) |
|---|---|
| Chelating agent | |
| EDTA-3Na 2H$_2$O | Appropriate amount |
| Activator | |
| Condensed PEG-1500 hydroxystearate | 0.5 |
| Condensed diglyceryl hydroxystearate | 1.5 |
| Oil component | |
| Isodecyl benzoate | 1.0 |
| Dineopentanoic acid tripropylene glycol | 4.5 |
| Dineopentanoic acid tripropylene glycol | 1.5 |
| Cetyl 2-ethylhexanoate | 3.0 |
| Diglycerol sorbitan tetra-2-ethylhexanoate | 5.0 |
| Decamethylcyclopentasiloxane | 10.0 |
| Trimethylsiloxy silicic acid - decamethylcyclopentasiloxane solution (50%) | 4.5 |
| 3,7-dimethyloctyl benzoate | 7.0 |
| UV absorbent | |
| Octylmethoxy cinnamate | 7.5 |
| Uvinul T150 (registered trademark) from BASF | 1.0 |
| Bisresorcinyl triazine {TINOSORB S (registered trademark) from Ciba Specialty} | 3.0 |
| UV scattering agent | |
| Hydrophobicized silica-coated zinc oxide | 15.0 |

(Preparation Method and Evaluation)

The ingredients are mixed and emulsified with a conventional method to obtain a W/O sunblock (cream). The obtained sunblock (cream) is superior in terms of refreshing sensation. It is also superior in terms of dissolution stability of ultraviolet absorbents.

Example 1-14 W/O Sunscreen (Emulsion)

| Water | |
|---|---|
| Ion-exchanged water | Balance |
| Humectant | |
| Dynamite glycerin | 5.0 |
| Thickener | |
| Succinoglycan | 0.35 |
| Carboxymethyl cellulose Na salt | 0.15 |
| Activator | |
| POE(100) hydrogenated castor oil | 1.5 |
| Scattering agent | |
| Condensed PEG-1500 hydroxystearate | 0.5 |
| Decamethylcyclopentasiloxane | 5.0 |
| Oil component | |
| Cetyl 2-ethylhexanoate | 2.0 |
| Glyceryl tri-2-ethylhexanoate | 3.0 |
| Isostearic acid | 1.0 |
| 3,7-dimethyloctyl benzoate | 5.0 |
| UV absorbent | |
| Octylmethoxy cinnamate | 5.0 |
| Uvinul T150 (registered trademark) from BASF | 2.0 |
| Bisresorcinyl triazine {TINOSORB S (registered trademark) from Ciba Specialty} | 3.0 |

-continued

| UV protection agent | |
|---|---|
| Hydrophobicized silica-coated zinc oxide | 15.0 |
| Ethanol | 5.0 |
| Preservative | |
| Methylparaben | Appropriate amount |

(Preparation Method and Evaluation)

The ingredients are mixed and emulsified with a conventional method to obtain a W/O sun protector (emulsion). The obtained sun protector (emulsion) is superior in terms of refreshing sensation. It is also superior in terms of dissolution stability of ultraviolet absorbents.

[Examples of the Skin Treatment Compositions of Claims 3-7]

The solubility of a slightly soluble ultraviolet absorbent in the alkyl benzoate obtained in the aforementioned synthetic examples 1-3 was measured. For the slightly soluble ultraviolet absorbent, a triazine-type ultraviolet absorbent 2,4-bis{[4-(2-ethylhexyloxy)-2-hydroxy]phenyl}-6-(4-methoxyphenyl)1,3,5-triazine was used.

The solubility is expressed as a concentration (mass percentage) in a saturated solution at 0° C.

For the alkyl benzoate having 12-15 carbon atoms, a commercial product (Crodamol AB from Croda, Inc.) was used. This oil component is a mixture of alkyl benzoates having 12-15 carbon atoms.

TABLE 2-1

| Oil components | Solubility |
|---|---|
| 2-ethylhexyl benzoate (Carbon number 8) | 12% |
| 3,5,5-trimethylhexyl benzoate (carbon number 9) | 13% |
| 3,7-dimethyloctyl benzoate (Carbon number 10) | 12% |
| Alkyl benzoate (Carbon number 12-15) | 8% |
| Di-2-ethylhexyl succinate | 4% |
| Pentaerythrite tetra (2-ethylhexanoate/paramethoxycinnamate) | 4% |
| Decamethyl cyclopentane siloxane | 0% |
| Liquid petrolatum | 0% |

Table 2-1 shows that the alkyl benzoates having 8-10 carbon atoms have a distinctively increased ability to dissolve slightly soluble drugs. Furthermore, 3,7-dimethyloctyl benzoate, which has 10 carbon atoms, turned out to be an excellent oil component without any odor.

However, in the present invention, a water-in-oil type emulsified composition that allows stable dissolution of slightly soluble ultraviolet absorbents at a desired blend ratio in the oil phase portion is expected to be obtained by preferably using alkyl benzoate having 8-10 carbon atoms.

Examples 2-1 to 2-8, Comparative Examples 2-1 to 2-8

Next, sunblock cosmetics consisting of the water-in-oil type emulsified compositions of Examples and Comparative examples shown in Table 2-2 and Table 2-3 were prepared and the following evaluations were conducted. The blend ratios are in % (mass percentage) units unless specified otherwise.

Manufacturing Methods of Examples 2-1 to 2-8 and Comparative Examples 2-1 to 2-8

(1)-(11) are mixed and stirred to obtain a homogeneous oil phase. (12) and (13) are then added to this oil phase and stirred homogeneously with a homomixer to obtain the oil phase portion. Finally, (15), dissolved in (14), is gradually added to the oil phase portion as it is stirred with the homomixer at room temperature (20° C.) to obtain a sunblock cosmetic (cream type).

"Refreshing Sensation on the Skin"

The refreshing sensation on the skin during use was evaluated with actual use testing by ten specialized panelists. The evaluation criteria are as follows:

◎ . . . Eight or more specialized panelists reported a refreshing sensation on the skin during use.
○ . . . Six or more and less than eight specialized panelists reported a refreshing sensation on the skin during use.
Δ . . . Three or more and less than six specialized panelists reported a refreshing sensation on the skin during use.
X . . . Less than three specialized panelists reported a refreshing sensation on the skin during use.

"Non-stickiness on the Skin"

The non-stickiness on the skin during use was evaluated with actual use testing by ten specialized panelists. The evaluation criteria are as follows:

◎ . . . Eight or more specialized panelists reported non-stickiness on the skin during use.
○ . . . Six or more and less than eight specialized panelists reported non-stickiness on the skin during use.
Δ . . . Three or more and less than six specialized panelists reported non-stickiness on the skin during use.
X . . . Less than three specialized panelists reported non-stickiness on the skin during use.

"Stability"

The samples were put into thermostatic baths kept at 50° C., 25° C., and −5° C., and observed microscopically or visually after three months.

◎ . . . No anomaly is observed microscopically or visually.
○ . . . No anomaly is observed visually but the microscopic observation reveals slight separation or crystalline precipitation.
Δ . . . Slight separation or crystalline precipitation is observed visually or microscopically.
X . . . Separation or crystalline precipitation is clearly observed visually.

"Ultraviolet Prevention Effect Test"

A highly accurate in vitro SPF measuring system (a system that can measure SPF values and PFA values with high accuracy) described in Japanese Patent Laid-Open No. H7-167781 bulletin was used.

Specifically, a solar simulator (Solar Ultraviolet Simulator Model 600 from Solar Light Co.) was used as the light source. 2.0 mg/cm$^2$ of the specimen was evenly applied on Transpore Tape™ (3M Co.) and ultraviolet light was irradiated on it. The transmitted ultraviolet light spectrum was processed to calculate the SPF value and the PFA value.

Table 2-2 and Table 2-3 show that Examples of the present invention are sunblock water-in-oil type emulsified cosmetics that have a high sunblock effect, give a refreshing sensation with no stickiness at the time of application, and exhibit superior stability.

The sunblock cosmetics obtained by using 3,5,5-trimethylhexyl benzoate and 2-ethylhexyl benzoate of synthetic example 2 and synthetic example 3, respectively, instead of 3,7-dimethyloctyl benzoate in Examples 2-1 to 2-8, also are sunblock water-in-oil type emulsified cosmetics that have a high sunblock effect, give a refreshing sensation with no stickiness at the time of application, and exhibit superior stability.

The sunblock cosmetics obtained by using tetraglycerin pentastearate or decamethyl pentaisostearate of general formula (3) instead of polyethylene glycol dipolyoxystearate in Examples 2-1 to 2-8, also are sunblock water-in-oil type emulsified cosmetics that have a high sunblock effect, give a refreshing sensation with no stickiness at the time of application, and exhibit superior stability.

TABLE 2-2

| Ingredient names | Examples | | | | | | | |
|---|---|---|---|---|---|---|---|---|
| | 2-1 | 2-2 | 2-3 | 2-4 | 2-5 | 2-6 | 2-7 | 2-8 |
| (1) Decamethylcyclopentasiloxane | — | — | — | 15.0 | — | — | — | — |
| (2) Dimethylpolysiloxane 6 mPa · s | — | — | — | — | — | — | — | — |
| (3) Di-2-ethylhexyl succinate | — | — | — | — | — | 19.5 | — | — |
| (4) 3,7-dimethyloctyl benzoate | 20.0 | 20.0 | 20.0 | 5.0 | 30.0 | 0.5 | 20.0 | 20.0 |
| (5) Polyethylene glycol dipolyhydroxystearate*[1] | 2.0 | — | 1.0 | 2.0 | 2.0 | 2.0 | 7.0 | 0.5 |
| (6) Decaglycerin pentaisostearate*[2] | — | 2.0 | 1.0 | — | — | — | — | — |
| (7) Polyether modified silicone*[3] | — | — | — | — | — | — | — | — |
| (8) Organically modified montmorillonite | — | — | — | — | — | — | — | — |
| (9) Bisresorcinyl triazine*[4] | 3.0 | 3.0 | 3.0 | 1.0 | 5.0 | 3.0 | 3.0 | 0.1 |
| (10) Octylmethoxy cinnamate | 7.0 | 7.0 | 7.0 | 9.0 | — | 7.0 | 7.0 | 9.9 |
| (11) Trimethylsiloxysilicic acid*[5] | 1.0 | 1.0 | 1.0 | 1.0 | 1.0 | 1.0 | 1.0 | 1.0 |

TABLE 2-2-continued

| Ingredient names | \multicolumn{8}{c}{Examples} | | | | | | | |
|---|---|---|---|---|---|---|---|---|
| | 2-1 | 2-2 | 2-3 | 2-4 | 2-5 | 2-6 | 2-7 | 2-8 |
| (12) Silicone-hydrophobicized titanium dioxide | 5.0 | 5.0 | 5.0 | 5.0 | 5.0 | 5.0 | 5.0 | 5.0 |
| (13) Silicone-hydrophobicized zinc oxide | 5.0 | 5.0 | 5.0 | 5.0 | 5.0 | 5.0 | 5.0 | 5.0 |
| (14) Ion-exchanged water | 56.85 | 56.85 | 56.85 | 56.85 | 51.85 | 56.85 | 51.85 | 58.35 |
| (15) Methylparaben | 0.15 | 0.15 | 0.15 | 0.15 | 0.15 | 0.15 | 0.15 | 0.15 |
| Refreshing sensation | ◎ | ◎ | ◎ | ◎ | ◎ | ◎ | ○ | ◎ |
| Non-stickiness | ◎ | ◎ | ◎ | ◎ | ◎ | ◎ | ○ | ○ |
| Stability | ◎ | ◎ | ◎ | ○ | ○ | ○ | ◎ | ○ |
| In Vitro SPF value | 51.3 | 50.6 | 51.5 | 46.4 | 52.1 | 47.3 | 49.5 | 50.2 |
| In Vitro PFA value | 8.3 | 8.1 | 8.3 | 5.4 | 8.6 | 6.7 | 7.9 | 8.0 |

[1] In general formula (2) for this compound, a is 5, b is 5, m is 30, and $R^1$ and $R^2$ are H.
[2] In general formula (3) for this compound, a is 5, b is 5, n is 10, and $R^1$ and $R^2$ are H.
[3] Product name: KF6017, 50% solution of decamethylcyclopentasiloxane, from Shin-Etsu Chemical Co., Ltd.
[4] Product name: TINOSORB S from Ciba Specialty
[5] Product name: KF7312J from Shin-Etsu Chemical Co., Ltd.

TABLE 2-3

| Ingredient names | \multicolumn{8}{c}{Comparative examples} | | | | | | | |
|---|---|---|---|---|---|---|---|---|
| | 2-1 | 2-2 | 2-3 | 2-4 | 2-5 | 2-6 | 2-7 | 2-8 |
| (1) Decamethylcyclopentasiloxane | 20.0 | — | 10.0 | 10.0 | 10.0 | 10.0 | — | — |
| (2) Dimethylpolysiloxane 6 mPa·s | — | — | — | 5.0 | 5.0 | — | — | — |
| (3) Di-2-ethylhexyl succinate | — | — | — | 5.0 | 5.0 | 10.0 | 20.0 | 20.0 |
| (4) 3,7-dimethyloctyl benzoate | — | 20.0 | 10.0 | — | — | — | — | — |
| (5) Polyethylene glycol dipolyhydroxystearate[1] | 2.0 | — | — | 2.0 | — | 2.0 | 7.0 | 1.0 |
| (6) Decaglycerin pentaisostearate[2] | — | — | — | — | 2.0 | — | — | 1.0 |
| (7) Polyether modified silicone[3] | — | 1.0 | 1.0 | — | — | — | — | — |
| (8) Organically modified montmorillonite | — | 1.0 | 1.0 | — | — | — | — | — |
| (9) Bisresorcinyl triazine[4] | 3.0 | 3.0 | 3.0 | 3.0 | — | — | 3.0 | 0.1 |
| (10) Octylmethoxy cinnamate | 7.0 | 7.0 | 7.0 | 7.0 | 10.0 | 10.0 | 7.0 | 9.9 |
| (11) Trimethylsiloxysilicic acid[5] | 1.0 | 1.0 | 1.0 | 1.0 | 1.0 | 1.0 | 1.0 | 1.0 |
| (12) Silicone-hydrophobicized titanium dioxide | 5.0 | 5.0 | 5.0 | 5.0 | 5.0 | 10.0 | 5.0 | 5.0 |
| (13) Silicone-hydrophobicized zinc oxide | 5.0 | 5.0 | 5.0 | 5.0 | 5.0 | 10.0 | 5.0 | 5.0 |
| (14) Ion-exchanged water | 56.85 | 56.85 | 56.85 | 56.85 | 56.85 | 46.85 | 51.85 | 57.0 |
| (15) Methylparaben | 0.15 | 0.15 | 0.15 | 0.15 | 0.15 | 0.15 | 0.15 | 0.15 |
| Refreshing sensation | ○ | ○ | ○ | ○ | ◎ | Δ | ○ | ○ |
| Non-stickiness | ○ | Δ | ○ | ○ | ◎ | Δ | ○ | ◎ |
| Stability | X | X | X | Δ | ○ | ◎ | X | Δ |
| In Vitro SPF value | 38.3 | 50.6 | 41.5 | 45.4 | 32.1 | 47.3 | 49.5 | 50.2 |
| In Vitro PFA value | 6.3 | 8.1 | 6.3 | 5.4 | 6.7 | 6.7 | 7.9 | 8.0 |

[1] In general formula (2) for this compound, a is 5, b is 5, m is 30, and $R^1$ and $R^2$ are H.
[2] In general formula (3) for this compound, a is 5, b is 5, n is 10, and $R^1$ and $R^2$ are H.
[3] Product name: KF6017 from Shin-Etsu Chemical Co., Ltd.
[4] TINOSORB S from Ciba Specialty
[5] Product name: KF7312J from Shin-Etsu Chemical Co., Ltd.

Other Examples of the present invention are shown below.

Example 2-9 Water-in-oil Type Sunblock Cosmetic

| (emulsion type) | % |
|---|---|
| (Oil phase portion) | |
| (1) Octyl-p-methoxycinnamate | 5.0 |
| (2) Oxybenzone | 3.0 |
| (3) 4-tert butyl-4'-methoxybenzoylmethane | 1.0 |
| (4) Silicone-hydrophobicized titanium dioxide | 6.0 |
| (5) Silicone-hydrophobicized zinc oxide | 6.0 |
| (6) Squalane | 10.0 |
| (7) Octyl benzoate | 23.0 |
| (8) Octamethylcyclotetrasiloxane | 5.0 |
| (9) Glycerin triisooctanoate | 2.0 |
| (10) Polyethylene glycol dipolyhydroxystearate (Represented by general formula (2) wherein a is 15, b is 15, m is 120, and $R^1$ and $R^2$ are methyl groups.) | 1.0 |
| (11) Bisresorcinyl triazin (Product name: TINOSORB S from Ciba Specialty Chemicals) | 3.0 |
| (Water phase portion) | |
| (12) Methylparaben | 0.1 |
| (13) Phenoxy ethanol | 0.1 |
| (14) Ion-exchanged water | 29.8 |
| (15) 1,3-butylene glycol | 5.0 |

Preparation Method

The ingredients of the oil phase portion and the water phase portion are separately heated up to 70° C. and dissolved. Dispersion of titanium dioxide in the oil phase is thoroughly conducted, to which the water phase portion is added as emulsification is carried out using a homogenizer. This emulsified composition is cooled with a heat exchanger to obtain an emulsion type water-in-oil type sunblock cosmetic having a viscosity of 8,000 MPa·s. The obtained sunblock cosmetic is refreshing and non-sticky; its SPF value is 50.1 and the PFA value is 8.8; and no anomaly is observed in the stability test after incubating for three months in thermostatic baths at −5° C., 25° C., and 50° C.

Example 2-10 Water-in-oil Type Sunblock Cosmetic

| (cream type) | % |
|---|---|
| (Oil phase portion) | |
| (1) Dextrin fatty acid ester-hydrophobicized titanium dioxide | 7.0 |
| (2) Silicone-hydrophobicized zinc oxide | 10.0 |
| (3) Decamethylcyclopentasiloxane | 10.0 |
| (4) 2-ethylhexyl benzoate | 25.0 |
| (5) Liquid petrolatum | 10.0 |
| (6) Glycerin triisooctanoate | 3.0 |
| (7) Tetraglycerin pentastearate | 4.0 |
| (8) Butylparaben | 0.2 |
| (9) Perfume | 0.1 |
| (10) Ethyl-4-isopropyl cinnamate | 5.0 |
| (11) Bisresorcinyl triazine (Product name: TINOSORB S from Ciba Specialty Chemicals) | 1.5 |

-continued

| (cream type) | % |
|---|---|
| (Water phase portion) | |
| (12) Ion-exchanged water | 21.7 |
| (13) 1,3-butylene glycol | 2.5 |

(Preparation Method)

The ingredients of the oil phase portion and the water phase portion are separately heated up to 70° C. and dissolved. Dispersion of titanium dioxide in the oil phase was thoroughly conducted, to which the water phase portion is added as emulsification is carried out using a homomixer. This emulsified composition is cooled with a heat exchanger to obtain a water-in-oil type sunblock cosmetic having a viscosity of 55,000 MPa·s.

The obtained sunblock cosmetic is refreshing and non-sticky; its SPF value is 49.2 and the PFA value is 8.3; and no anomaly is observed in the stability test after incubating for three months in thermostatic baths at −5° C., 25° C., and 50° C.

Example 2-11 Water-in-oil Type Sunblock Cosmetic

| (emulsion type) | % |
|---|---|
| (Oil phase portion) | |
| (1) Dimethylpolysiloxane (6 mPa · s) | 12.0 |
| (2) 3,7-dimethyloctyl benzoate | 25.0 |
| (3) Liquid petrolatum | 1.5 |
| (4) Octylmethoxy cinnamate | 7.0 |
| (5) Ethylparaben | 0.2 |
| (6) Perfume | 0.1 |
| (7) Dextrin fatty acid ester-hydrophobicized zinc oxide | 6.0 |
| (8) Polyethylene glycol dipolyhydroxystearate (Represented by general formula (2) wherein a is 7, b is 7, m is 35, and $R^1$ and $R^2$ are H.) | |
| (Water phase portion) | |
| (9) Ion-exchanged water | 39.7 |
| (10) Propylene glycol | 5.0 |
| (12) Sodium glutamate | 1.5 |
| (13) Sodium chloride | 0.5 |

(Preparation Method)

The ingredients of the oil phase portion and the water phase portion are separately heated up to 70° C. and dissolved. Dispersion of titanium dioxide in the oil phase was thoroughly conducted, to which the water phase portion is added as emulsification is carried out using a homogenizer. This emulsified composition is cooled with a heat exchanger to obtain an emulsion type water-in-oil type sunblock cosmetic having a viscosity of 2000 MPa·s. The obtained sunblock cosmetic is refreshing and non-sticky; its SPF value is 42.4 and the PFA value is 6.8. No anomaly is observed in the stability test after incubating for three months in thermostatic baths at −5° C., 25° C., and 50° C.

INDUSTRIAL APPLICABILITY

The alkyl benzoate having a specific structure used in the present invention is preferably used in a skin treatment composition as an oil component that gives a refreshing sensation at the time of application and can contain drugs and ultraviolet absorbents in a stable manner.

The present invention can provide a skin treatment composition that gives a superior refreshing sensation at the time of application and can contain slightly soluble ultraviolet absorbents and drugs without difficulty.

The sunblock cosmetic of the present invention, in spite of being a water-in-oil type emulsified composition, can contain a highly polar ultraviolet absorbent in a stable manner and also gives an excellent refreshing and non-sticky sensation at the time of application.

The present invention makes it possible to easily manufacture a sunblock cosmetic that can exhibit desired ultraviolet prevention effects, superior stability, and superior sensation at the time of application.

The invention claimed is:

1. A skin treatment composition comprising an alkyl benzoate represented by the following general formula (1):

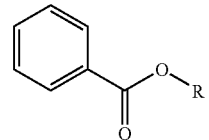
(1)

wherein R denotes a branched or straight chain alkyl group having 8-10 carbon atoms.

2. The skin treatment composition of claim 1 wherein the compound represented by the aforementioned general formula (1) is 3,7-dimethyloctyl benzoate.

* * * * *